(12) United States Patent
Goebel et al.

(10) Patent No.: US 12,053,153 B2
(45) Date of Patent: *Aug. 6, 2024

(54) ENDOSCOPE HAVING AN OPTICAL WAVEGUIDE WITH EMERGENCE PORTION AN OBJECTIVE BEAM SPLITTER

(71) Applicants: Karl Storz SE & Co. KG, Tuttlingen (DE); GRINTECH GmbH, Jena (DE)

(72) Inventors: Werner Goebel, Tuttlingen (DE); Bernhard Messerschmidt, Jena (DE)

(73) Assignees: Karl Storz SE & Co. KG, Tuttlingen (DE); GRINTECH GmbH, Jena (DE)

( * ) Notice: Subject to any disclaimer, the term of this patent is extended or adjusted under 35 U.S.C. 154(b) by 1006 days.

This patent is subject to a terminal disclaimer.

(21) Appl. No.: 16/918,635

(22) Filed: Jul. 1, 2020

(65) Prior Publication Data
US 2020/0329954 A1    Oct. 22, 2020

Related U.S. Application Data

(63) Continuation of application No. 15/046,957, filed on Feb. 18, 2016, now Pat. No. 10,736,489.

(30) Foreign Application Priority Data

Feb. 18, 2015   (DE) ..................... 10 2015 002 084.6

(51) Int. Cl.
*A61B 1/00*   (2006.01)
*A61B 1/05*   (2006.01)
(Continued)

(52) U.S. Cl.
CPC ............ *A61B 1/00096* (2013.01); *A61B 1/05* (2013.01); *A61B 1/07* (2013.01); *G02B 23/243* (2013.01); *G02B 23/2469* (2013.01)

(58) Field of Classification Search
CPC ......... A61B 1/05; A61B 1/07; A61B 1/00096; A61B 1/00163; A61B 1/00165;
(Continued)

(56) References Cited

U.S. PATENT DOCUMENTS

| 4,671,630 | A  | 6/1987  | Takahashi |
| 6,485,413 | B1 | 11/2002 | Boppart et al. |

(Continued)

FOREIGN PATENT DOCUMENTS

| DE | 10 2006 046 555 B4 | 12/2010 |
| EP | 0 096 570 A1       | 12/1983 |

(Continued)

OTHER PUBLICATIONS

British Search Report for British Application No. GB1602876.3 dated Jul. 21, 2016.

*Primary Examiner* — Timothy J Neal
*Assistant Examiner* — William B Chou
(74) *Attorney, Agent, or Firm* — Muncy, Geissler, Olds & Lowe, P.C.

(57) ABSTRACT

An endoscope having an elongate shaft, an objective arranged in a distal end region of the shaft for generating an image of an object field in an image plane. The objective having a beam splitter, and an image recorder for recording the image of the object field and an optical waveguide for forwarding illumination radiation from a proximal region to the distal end region of the shaft. The endoscope being embodied as a contact endoscope, a sensor area of the image recorder arranged in the image plane and an emergence portion of the optical waveguide adapted to forward at least some of the illumination radiation to the beam splitter to illuminate the object field.

20 Claims, 4 Drawing Sheets

(51) Int. Cl.
*A61B 1/07* (2006.01)
*G02B 23/24* (2006.01)

(58) Field of Classification Search
CPC .............. A61B 1/00167; A61B 1/0017; A61B
1/00174; A61B 1/00179; A61B 1/00181;
A61B 1/00183; A61B 1/00188; A61B
5/0084; G02B 23/243
See application file for complete search history.

(56) References Cited

U.S. PATENT DOCUMENTS

| | | | |
|---|---|---|---|
| 7,511,891 B2 | 3/2009 | Messerschmidt | |
| 7,662,095 B2 | 2/2010 | Irion | |
| 2002/0027723 A1* | 3/2002 | Lei | G02B 23/243 |
| | | | 359/691 |
| 2005/0277810 A1 | 12/2005 | Irion | |
| 2006/0241496 A1 | 10/2006 | Fengler et al. | |
| 2009/0009759 A1 | 1/2009 | Backman et al. | |
| 2010/0053312 A1* | 3/2010 | Watanabe | A61B 1/00181 |
| | | | 348/E7.085 |
| 2014/0066756 A1* | 3/2014 | Sinclair | A61B 5/0077 |
| | | | 264/1.24 |

FOREIGN PATENT DOCUMENTS

| | | |
|---|---|---|
| EP | 1 545 290 B1 | 10/2007 |
| JP | H06-34889 A | 2/1994 |
| JP | 2002-023067 A | 1/2002 |
| JP | 2011-245019 A | 12/2011 |
| WO | WO2011/148784 A1 | 12/2011 |
| WO | WO 2016/019235 A1 | 2/2016 |

* cited by examiner

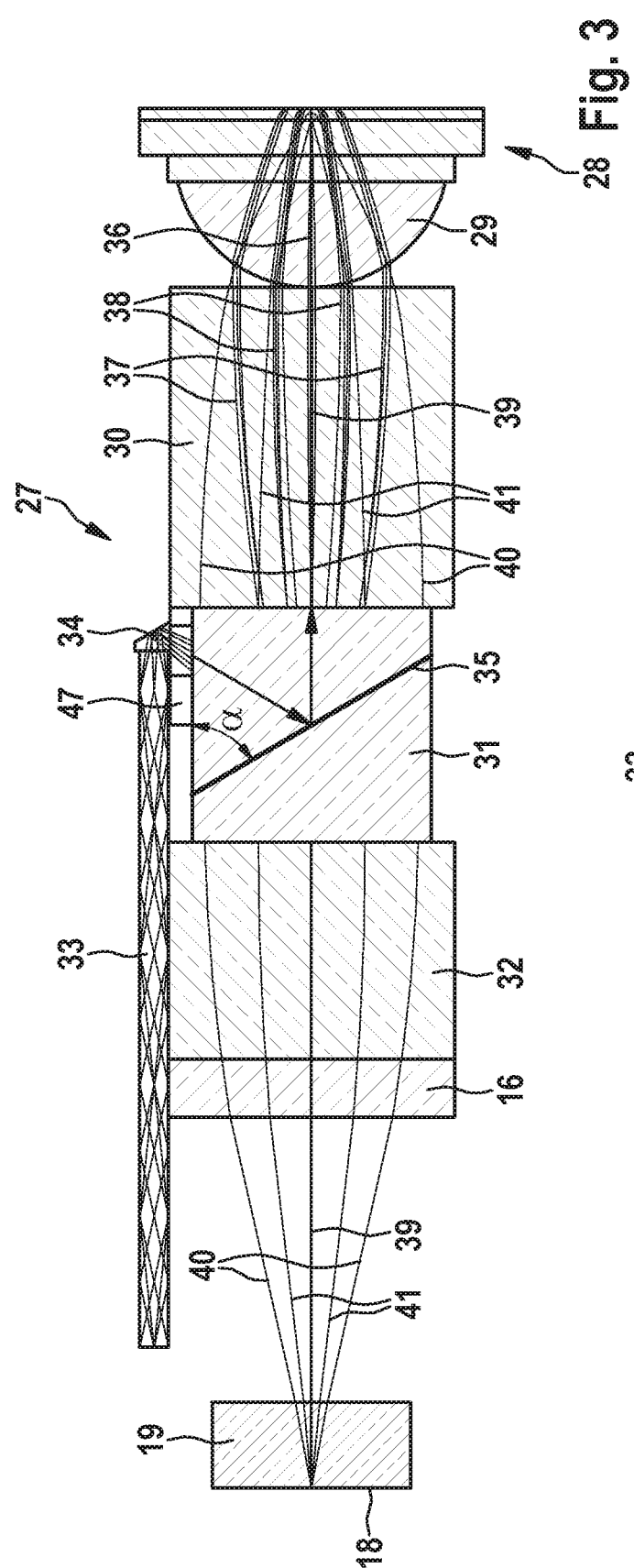
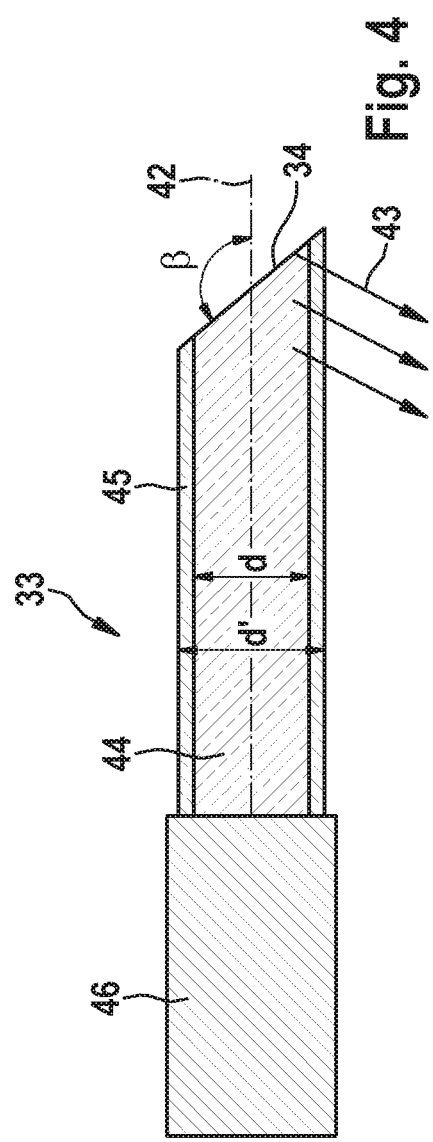

ENDOSCOPE HAVING AN OPTICAL WAVEGUIDE WITH EMERGENCE PORTION AN OBJECTIVE BEAM SPLITTER

This nonprovisional application is a continuation of U.S. application Ser. No. 15/046,957 filed on Feb. 18, 2016, which claims priority under 35 U.S.C. § 119(a) to German Patent Application No. DE 10 2015 002 084.6, which was filed in Germany on Feb. 18, 2015, and which is herein incorporated by reference.

BACKGROUND OF THE INVENTION

Field of the Invention

The present invention relates to an endoscope.

Description of the Background Art

Endoscopic examination techniques have prevailed in a multiplicity of medical and veterinary fields of application. Here, an endoscope, which has an elongate shaft with an imaging optical system, is introduced into the interior of the body, for example into a cavity in the interior of the body, in order to record an image of an object field there and to transmit said image to outside of the body and thereby make it available for observation or evaluation. Increasingly, use is made of video endoscopes which have an electronic image recorder for recording the image of the object field.

In many cases, an examination of the tissue is essential for a reliable diagnosis. Contact endoscopes are known for this purpose; they have an optical system designed for contact with tissue to be examined in order to enable high-resolution imaging. In order to illuminate the object field, the illumination light generated by a light source arranged in the proximal region of the endoscope is usually guided with the aid of optical fibers to the distal end of the shaft of the endoscope, where it emerges distally, substantially in the axial direction. As a result of the small distance from the object field, a sufficiently bright and/or sufficiently homogeneous illumination of the object field often cannot be achieved in the case of contact endoscopes. For example, this applies to fluorescence examinations, wherein fluorescence excitation radiation is radiated in a short-wavelength wavelength range onto a tissue region to be examined and the fluorescence radiation emitted by the tissue is observed in a longer-wavelength wavelength range. At the same time, the admissible external diameter of the endoscope is very restricted in many applications, and so a miniaturized embodiment of the imaging optical system and of the illumination system is required.

DE 10 2006 046 555 B4, which corresponds to U.S. Pat. No. 7,511,891, which is incorporated herein by reference, describes a miniaturized optically imaging system with a high lateral and axial resolution, which is designed for endoscopic applications for example. The miniaturized optically imaging system comprises a refractive planoconvex homogeneous optical lens which, with the plane side thereof, defines a plane entry surface of the optical system, a first GRIN (Gradient-Index) lens for reducing the divergence of the light beam transmitted from the object field through the refractive lens and a second GRIN lens for adapting the light beam transmitted by the first GRIN lens to a subsequent optical transmission system to a sensor unit. Compared to the transmission length, the transmission system has a small diameter and it is embodied as e.g. a flexible image-guiding fiber bundle or as rigid relay optics. For the purposes of coupling light, a thin excitation fiber is arranged along the optical axis. For the purposes of fluorescence observations, a deflection element embodied as a beam splitter can be arranged between the first and the second GRIN lens, wherein the beam splitter has a dichroic beam-splitting coating, which passes the excitation light in transmission and deflects the radiation emitted by the object in a reflecting manner.

EP 1 545 290 B1, which corresponds to U.S. Pat. No. 7,662,095, which is incorporated herein by reference, discloses an endoscope for illuminating and observing object fields in cavities, which has an illumination unit and an image transmission system, assigned to which there is an objective on the distal side and eyepiece or camera optics as an observation system on the proximal side. An optical splitter element for mutually complementary light polarizations or wavelength regions and light polarizations is inserted on the proximal side between the illumination unit, the image transmission system and the observation system in such a way that the illumination light generated by the illumination unit can be coupled into the image transmission system.

SUMMARY OF THE INVENTION

It is an object of the present invention to provide an endoscope that enables an improved illumination of an object field, for example of a tissue region in contact with a distal window of the endoscope, and a resolution that is as high as possible and loss-free imaging and, at the same time, which is embodied with a diameter that is as small as possible in this case.

An endoscope according to an exemplary embodiment of the invention comprises an elongate shaft which, for example, is suitable for insertion into a cavity in the interior of the body or for insertion into an external shaft insertable into such a cavity or into human or animal tissue or into a work channel of an endoscope or of an endoscopic instrument. The shaft can be embodied with a small diameter of approximately one to a few millimeters and, compared therewith, a substantially greater length. By way of example, the shaft can also be suitable for insertion into a biopsy needle. The shaft can have a rigid embodiment, but it can also be semi-rigid or flexible.

Arranged in a distal end region of the shaft is an objective for imaging an object field into an image plane which, for example, is the first image plane in the beam path of the imaging optics. The object field can be a surface region in a cavity in the interior of the body, into which the shaft of the endoscope was inserted. The object field can be a region of human or animal tissue in contact with a distal end region of the shaft, for example with an entry window of the objective. An endoscope embodied for observing tissue in contact with the distal end region of the shaft can also be referred to as a "contact endoscope." Even if an object field or a tissue region to be observed is not in direct contact with an entry window of the objective but has a small distance therefrom of e.g. less than approximately 100 µm, this can also be referred to as "contact" in the present context. The endoscope according to the invention is embodied as a contact endoscope. For example, the endoscope according to the invention is embodied in such a way that the object field or an object plane, which is arranged at a distance of less than 200 µm, for example, at a distance of less than approximately 100 µm from an entry surface of the objective, for example the entry window, is imaged in the image plane.

The present invention can also be advantageous in the case of endoscopes which are not embodied as contact endoscopes.

The objective comprises a beam splitter. The beam splitter is arranged in the beam path of the light entering into the objective from the object field in front of the image plane and it can be embodied e.g. as a splitter cube. The beam splitter can be arranged in a region of the beam path of the objective in which the observation beam path, i.e. the beam path of the light coming from the object field and imaged in the image plane, is approximately parallel. For example, the beam splitter has a beam-splitting splitter surface that is at an angle to an optical axis of the objective.

Furthermore, the endoscope according to an embodiment of the invention has an electronic image recorder or an optoelectronic image transducer which serves to record the image of the object field generated in the image plane. Therefore, the endoscope is embodied as a video endoscope. For example, the image recorder can be connectable by way of an electric line to a supply, display and/or storage apparatus in order to operate the image recorder and display the recorded image of the object field, which for example depicts tissue that is in contact with the distal end region of the shaft, to a user and provide it for a further evaluation.

Furthermore, the endoscope comprises an optical waveguide for forwarding illumination radiation from a proximal region of the shaft to the distal end region of the shaft. For example, the proximal region of the shaft can be a proximal end region of the shaft. In the proximal region of the shaft, a light source can be arranged or connectable to the endoscope, wherein the light source may comprise for example a white-light source, for example a xenon lamp, a superluminescence diode, a light-emitting diode and/or a laser light source, the light of which is coupled into the optical waveguide. The optical waveguide can be formed by one or more optical fibers. Within the scope of the present invention, "radiation" is understood to mean visible light for example, but also radiation in the ultraviolet or infrared spectral range. Here, the expression "light" also relates to both visible light and the adjacent spectral ranges.

According to the invention, a sensor area of the image recorder is arranged in the image plane of the objective in order to record the image of the object field generated by the objective. The image recorder is therefore arranged in the distal end region of the shaft; such endoscopes are also referred to as "chip on the tip endoscopes". By way of example, the image recorder can be a CCD or a CMOS sensor.

Furthermore, according to the invention, the optical waveguide has an emergence portion, wherein the emergence portion is arranged and embodied to forward at least some of the illumination radiation to the beam splitter. The beam splitter is arranged and embodied to couple at least some of the illumination radiation forwarded by the emergence portion to the beam splitter into a beam path of the objective for illuminating the object field.

As a result of the sensor area of the image recorder being arranged in the image plane of the objective and hence in the distal end region of the shaft, it is possible to dispense with an optical image transmission system. As a result of this, it is possible to avoid those light losses which would be suffered in the case where the image generated by the objective is transmitted to the proximal end region of the endoscope by way of such an image transmission system which, for example, comprises relay lenses or a coherent bundle of optical fibers. As a result of the arrangement, according to the invention, of the objective and the image recorder, it is possible for a high numerical aperture and hence a high resolution to be obtainable. Furthermore, as a result of an emergence portion of the optical waveguide and the beam splitter arranged in the objective being embodied to forward at least some of the illumination radiation to the object field, it becomes possible to couple illumination radiation into the beam path of the objective and to radiate said illumination radiation onto the object field from the direction of an optical axis of the objective, as a result of which improved illumination is achievable. For example, a brighter and more homogeneous illumination of the object field, and hence a brighter and more homogeneous image, can be achieved thereby. Furthermore, a particularly high degree of miniaturization of the distal end region of the shaft of the endoscope can be obtainable thereby and the endoscope shaft can be realizable with a very small diameter, for example when using a correspondingly miniaturized image recorder. By way of example, an endoscope according to the invention can be embodied in such a way that it can be inserted into a work channel of another endoscope or of an endoscopic instrument and used together with the latter or it can be integrated into such an instrument, for example into biopsy forceps.

In accordance with an exemplary embodiment of the invention, the emergence portion of the optical waveguide is embodied to forward at least some of the illumination radiation in an axial direction and the beam splitter is embodied to pass at least some of the illumination radiation in the axial direction to illuminate the object field and to deflect at least some radiation coming from the object field. In accordance with this embodiment, the object field is therefore illuminated substantially without deflection, i.e. the part of the illumination radiation forwarded from the emergence portion of the optical waveguide to the beam splitter is forwarded in the direction of the axis of the endoscope to the beam splitter and it is at least partly passed by the latter for the purposes of illuminating the object field in the axial direction. The emergence portion of the optical waveguide can be a distal end surface of the optical waveguide which is substantially perpendicular to the longitudinal axis of the optical waveguide. In this embodiment, the observation beam path comprises a deflection, wherein at least some of the observation radiation coming from the object field is deflected by the beam splitter in the direction of the image recorder. In this case, the image recorder is arranged in such a way that the part of the radiation entering into the objective from the object field, deflected by the beam splitter, is imaged on the sensor area. For example, the image plane of the objective can be arranged in such a way here that the direction of the normal of the image plane is perpendicular to the longitudinal axis of the endoscope, i.e. the sensor area of the image recorder, with the normal direction thereof, is likewise arranged perpendicular to the longitudinal axis. Hence, the image recorder is received in the shaft of the endoscope whilst "lying". As a result of this, an arrangement with a particularly high degree of miniaturization is made possible, particularly when using an image recorder with a rectangular sensor area with two edges of different length. As a result of this, an illumination substantially coaxial with the observation beam path is furthermore made possible thereby, allowing a particularly bright and uniform illumination of the object field.

In accordance with a particularly preferred embodiment of the invention, the emergence portion of the optical waveguide is embodied to deflect at least some of the illumination radiation from an axial into an off-axis direction pointing to the beam splitter. The beam splitter is embodied and arranged to deflect at least some of the illumination radiation forwarded from the emergence portion to the beam splitter in the direction of the object field for the purposes of illuminating the object field, i.e. the part of the illumination radiation deflected by the beam splitter is coupled into the beam path of the objective and forwarded in the distal direction to the object field. Furthermore, the beam splitter is embodied in such a way that at least some of the radiation entering into the objective from the object field is formed in an axial direction to the image recorder. In accordance with this embodiment, the object field is therefore illuminated by way of a deflection in the emergence portion of the optical waveguide by way of a further deflection in the beam splitter, as a result of which at least some of the illumination radiation is coupled into the beam path of the objective in the axial direction. Secondly, the observation beam path is not deflected in the beam splitter but the image recorder is arranged in such a way that the part of the radiation entering into the objective from the object field passed by the beam splitter is imaged on the sensor area. In this case, the image plane of the objective can be arranged, for example, in such a way that the normal direction of the image plane is substantially parallel to the longitudinal axis of the endoscope, i.e. the sensor area of the image recorder is arranged substantially perpendicular to the longitudinal axis. As a result of this, an efficient illumination of the object field and an observation with a high resolution is made possible in a simple manner.

Advantageously, the emergence portion comprises an at least partly reflecting, e.g. partly mirrored, deflection surface that is at an angle to a longitudinal axis of the optical waveguide, which deflection surface is embodied to deflect at least some of the illumination radiation to the beam splitter. The deflection surface can be embodied as a substantially plane area, the normal of which is in a direction directed at an angle to the longitudinal axis of the shaft and hence an angle to the longitudinal axis of the optical waveguide.

The optical waveguide comprises at least one optical fiber and the deflection surface can be an oblique end surface of the at least one optical fiber. For example, the optical waveguide can comprise exactly one optical fiber, with the aid of which illumination radiation is guided from the proximal region of the shaft to the distal end region, and the deflection surface is an obliquely whetted end surface of the optical fiber. As a result of this, a deflection of at least some of the illumination radiation in the direction of the beam splitter for the purposes of coupling into the beam path of the objective is made possible in a particularly simple manner. The end surface of the optical fiber can be at least partly mirrored in such a way that at least some of the illumination radiation is deflected by reflection at the end surface. As a result of the deflection surface being an oblique end surface of the at least one optical fiber, a particularly high degree of miniaturization is made possible in a simple manner. Furthermore, a particularly cost-effective production is possible since there is no need for a further deflecting component. Furthermore, it is generally not necessary to remove the cladding of the optical fiber; instead, the forwarding of the part of the illumination light deflected at the deflection surface can be through the cladding since there is no total-internal reflection at the boundary between the core and the cladding due to the larger angle with respect to the longitudinal axis of the optical fiber. Alternatively, the emergence portion of the optical waveguide can be embodied as, for example, a deflection prism or a splitter cube.

In a particularly advantageous manner, the deflection surface of the optical waveguide and the splitter surface of the beam splitter are each formed by a plane surface, with the surfaces being parallel or substantially parallel to one another. The longitudinal axis of the at least one optical fiber of the optical waveguide, in the distal end region of the optical waveguide, can extend substantially parallel to the longitudinal axis of the shaft, in the distal end region of the shaft, such that the directions of the normals of the deflection surface of the optical waveguide and the splitter surface of the beam splitter include the same angle with the longitudinal axis of the shaft, which angle can lie, for example, in the region from approximately 30° to approximately 45°. Both surfaces are therefore at an angle to the longitudinal axis of the endoscope with the same angle, wherein the normal directions of the deflection surface of the optical waveguide and the mirror surface of the beam splitter and the longitudinal axes of the shaft and of the optical fiber lie in one plane. As a result of this, a particularly efficient light deflection and a particularly compact design and a particularly high degree of miniaturization are made possible. For example, the deflection surface of the optical waveguide and the splitter surface of the beam splitter can be arranged in such a way that an illumination beam extending along the central longitudinal axis of the optical fiber is coupled approximately into the optical axis of the objective. As a result of this, a coaxial illumination which enables a particularly high light transmission and uniform illumination of the object field in a simple manner can be realized.

In accordance with a particularly preferred embodiment of the invention, the at least one optical fiber of the optical waveguide, in the distal end region thereof, extends substantially parallel to the shaft of the endoscope, in the distal end region thereof, and the surface normal of the deflection surface of the optical waveguide forms an angle of more than 0° and less than 90°, for example between 20° and 50°, or between 30° and 45°, for example approximately 30° or 45° with the longitudinal axis of the optical waveguide or of the shaft. At least some of the illumination light is therefore reflected at an angle of for example between 40° and 100°, or between 60° and 90°, more particularly at an angle of approximately 60° or 90° with respect to the longitudinal axis of the endoscope. Furthermore, in accordance with this embodiment of the invention, the normal of the splitter surface of the beam splitter likewise includes an angle of, for example, between 20° and 50°, or between 30° and 45°, more particularly approximately 30° or 45° with a longitudinal axis of the shaft such that the part of the illumination light forwarded by the deflection surface to the beam splitter is deflected at the splitter surface of the beam splitter by the same angle as at the deflection surface of the optical waveguide, for example likewise by approximately 60° or 90°, and thereby forwarded to the object field in the distal direction substantially parallel to the longitudinal axis of the shaft. In a particularly advantageous manner, the deflection surface of the optical waveguide and the splitter surface of the beam splitter can be arranged in such a way that an illumination beam extending along the central longitudinal axis of the optical fiber is coupled approximately into the optical axis of the objective and hence coaxially into the beam path of the objective. As a result of this, particularly efficient forwarding of the illumination light to the object field and particularly bright and uniform illumination of the object field are made possible.

In accordance with an exemplary embodiment of the invention, the deflection surface of the optical waveguide has a dichroic beam-splitting embodiment, for example as an oblique end surface, provided with a dichroic coating, of at least one optical fiber of the optical waveguide. For example, the deflection surface of the optical waveguide is embodied to pass some of the illumination radiation, wherein the passed part of the illumination radiation can be e.g. received by a further optical waveguide and forwarded to the object field. The part of the illumination radiation which was transmitted and forwarded to the object field can be used, for example, for a white-light illumination of the object field, while the component reflected to the beam splitter by the deflection surface can be fluorescence excitation radiation. As a result of this, additional observation possibilities are created, wherein the beam-splitting properties of the deflection surface and, optionally, of the beam splitter may be selected in such a way that both observation of the fluorescence radiation and white-light observation are possible. To this end, the image recorder can be embodied to distinguish between various wavelength ranges, for example as a color sensor.

As an alternative or in addition to a beam-splitting embodiment of the deflection surface of the optical waveguide, a further optical waveguide may be present, the latter being embodied to forward a further part of the illumination radiation from the proximal region of the shaft to the distal end region of the shaft of the endoscope and, for example, enabling additional white-light illumination. As a result of this too, further observation possibilities can be created in an advantageous manner.

An optical coupling element for improving the coupling of the part of the illumination radiation emerging from the emergence portion to the beam splitter into the beam splitter and hence into the beam path of the objective can be arranged between the emergence portion of the optical waveguide and the beam splitter. The optical coupling element consists, for example, of a transparent material which has a refractive index adapted to the refractive index of the emergence portion of the optical waveguide and/or of the beam splitter. The coupling element can adjoin the emergence portion of the optical waveguide and the beam splitter tightly and/or it can be cemented to the emergence portion of the optical waveguide and/or the beam splitter. By way of example, the optical coupling element can comprise a plane-parallel plate or consist of a transparent potting compound. The optical coupling element can have a plane surface adjoining the beam splitter and a negative cylindrical surface adjoining the emergence portion of the optical waveguide, for example at the distal end region of an optical fiber of the optical waveguide. As a result of this, light losses and unwanted refractive effects during the emergence of the illumination radiation from the optical waveguide and during the coupling of the part of the illumination radiation emerging from the emergence portion into the beam splitter can be avoided or at least reduced.

The beam splitter can be embodied as a prism beam splitter, for example as a beam splitter cube, or else as a beam splitter plate. As a result of this, a compact and robust design, and also simple production, are made possible. Here, the production of an endoscope with a beam splitter plate is possible in a particularly cost-effective manner, particularly if the splitter surface is at an angle of approximately 45° with respect to the optical axis or with respect to the longitudinal axis of the shaft.

In accordance with an exemplary embodiment of the invention, the beam splitter can be embodied as a polarizing beam splitter in such a way that a light component with a first polarization is at least predominantly reflected at the splitter surface and a light component with a polarization complementary to the first polarization is at least predominantly passed by the splitter surface. For example, the first polarization and the polarization complementary thereto can be mutually perpendicular linear polarizations. As a result of this, it becomes possible to separate differently polarized components of the light coming from the object field from one another. This is advantageous, for example, if, within the scope of a fluorescence observation, polarized excitation radiation is radiated onto the tissue to be examined and at least partly unpolarized fluorescence radiation is observed. Then, the polarization of the excitation radiation can be selected in such a way that the excitation radiation is at least predominantly reflected by the beam splitter in the direction of the object field, but at least some of the fluorescence radiation is passed by the beam splitter in the direction of the image recorder. As a result of this, a large part of the reflected or scattered excitation radiation reaching the objective from the object field can be eliminated, just like a large part of reflected or scattered excitation radiation created within the objective. In this way, a largely undisturbed observation of the fluorescence radiation can be made possible and the quality of the recorded fluorescence image can be improved.

In accordance with an embodiment of the invention, the beam splitter is embodied to split beams in a dichroic manner and, for example, to forward at least some of the illumination radiation in a shorter-wavelength wavelength range to the object field and to forward at least some of the radiation coming from the object field in a longer-wavelength wavelength range to the image recorder. This is advantageous, for example, in the case where the endoscope is a fluorescence endoscope and the optical waveguide, the emergence portion of the optical waveguide and the beam splitter are embodied to forward fluorescence excitation radiation to the object field and the objective and the image recorder are embodied to record fluorescence radiation generated by the tissue situated in the object field. Here, the shorter-wavelength wavelength range is the wavelength range of radiation suitable for exciting the fluorescence and the longer-wavelength wavelength range is that of the fluorescence radiation generated by the tissue. To this end, the beam splitter can have a splitter surface with a dichroic coating, wherein the dichroic coating can be adapted to at least one fluorescence mode to be observed or one fluorescence substance. This renders it possible to largely eliminate the excitation radiation reflected in the object field, which is typically brighter than the weak fluorescence radiation by orders of magnitudes and which would mask the latter without further measures, and this allows an undisturbed observation of the fluorescence of the tissue. In accordance with a further embodiment of the invention, the beam splitter can have both a dichroic and a polarizing embodiment in a corresponding manner, as a result of which a further improvement in the quality of the recorded fluorescence image is made possible.

Further, the objective can have a filter for blocking fluorescence excitation radiation and for passing fluorescence radiation, said filter being arranged between the beam splitter and the sensor area of the image recorder. By way of example, the filter can be embodied as an edge filter. The filter can be arranged in a region of the objective with a parallel or substantially parallel beam path, which is advantageous, particularly if the filter is an interference filter. However, it is also possible to arrange the filter in a different part of the beam path of the objective between the splitter surface of the beam splitter and the sensor area of the image recorder, particularly in the convergent part of the beam path. This enables a further improvement in the separation of excitation and fluorescence radiation and a further improvement in the quality of the recorded fluorescence image.

In an embodiment, the objective comprises one or more gradient index (GRIN) lenses. This enables a particularly compact embodiment of the objective with a high resolution and a particularly simple assembly of the objective. For example, the objective can comprise a first and second GRIN lens, wherein the beam splitter is arranged between the first and the second GRIN lens in a substantially parallel part of the beam path of the objective. By way of example, the objective can be embodied with exactly two such GRIN lenses and a planoconvex lens disposed upstream thereof on the distal side. By way of example, such an embodiment of the objective is disclosed in DE 10 2006 046 555 B4, which document, in this respect, is herewith included in the present application by reference.

The objective can be embodied in such a way that a magnification lies in a range from approximately 0.5 to 5. Here, the magnification is the ratio of the image size, i.e. the size of the image cast on the sensor area of the image recorder, to the size of the imaged object. Such a magnification range is advantageous, for example, for the contact-endoscopic examination of tissue.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein:

FIG. 3 shows a schematic illustration of an objective with an illumination system of an endoscope in accordance with a second exemplary embodiment of the invention;

FIG. 4 shows the distal end region of the optical waveguide in the exemplary embodiment in accordance with FIG. 3;

DETAILED DESCRIPTION

Figure 1:
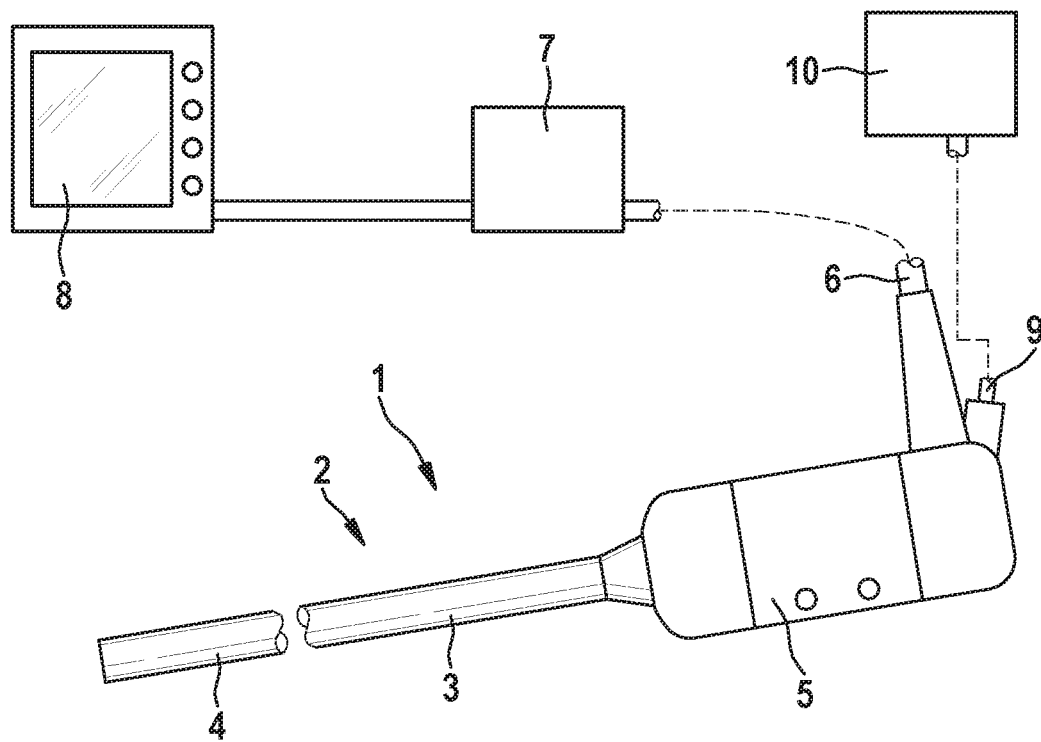
FIG. 1 shows a schematic overall illustration of an endoscopic system with an endoscope in accordance with an exemplary embodiment of the invention.

FIG. 1 depicts, in a schematic form, an endoscopic system which comprises an endoscope 1 embodied in accordance with an exemplary embodiment of the invention. The endoscope 1 has an elongate shaft 2 which, in the shown exemplary embodiment, is embodied with a rigid shaft tube 3; alternatively, an endoscope according to the invention could have a semi-rigid or flexible shaft. The distal end region of the shaft 2 is denoted by the reference sign 4 in FIG. 1. Arranged at the proximal end of the shaft 2, the endoscope 1 furthermore comprises a handpiece 5 which remains outside of the body in the case of an endoscopic intervention. Arranged within the shaft 2 is an electronic image recorder (not depicted here). By way of an electric cable 6, the handpiece 5 is connected to a supply apparatus 7 which serves to actuate electronic components in the interior of the endoscope 1 and process and store the endoscopic image recorded by the endoscope 1. Connected to the supply apparatus 7 is a monitor 8 for displaying the endoscopic image to a user. Furthermore, the handpiece 5 is connected to a light source unit 10 by way of an optical waveguide cable 9. By way of example, the light source unit 10 comprises a xenon lamp for generating the illumination radiation, which can serve both for white-light illumination and for fluorescence excitation; by way of example, provision can also be made for a laser light source for generating the fluorescence excitation radiation and/or a superluminescence diode. The electric cable 6 and the optical waveguide cable 9 can be detachably connected to the handpiece 5 by way of connection means (not depicted in FIG. 1). The endoscope 1 is embodied as a contact endoscope. Embodiments of the endoscope 1 are described below.

Figure 2:
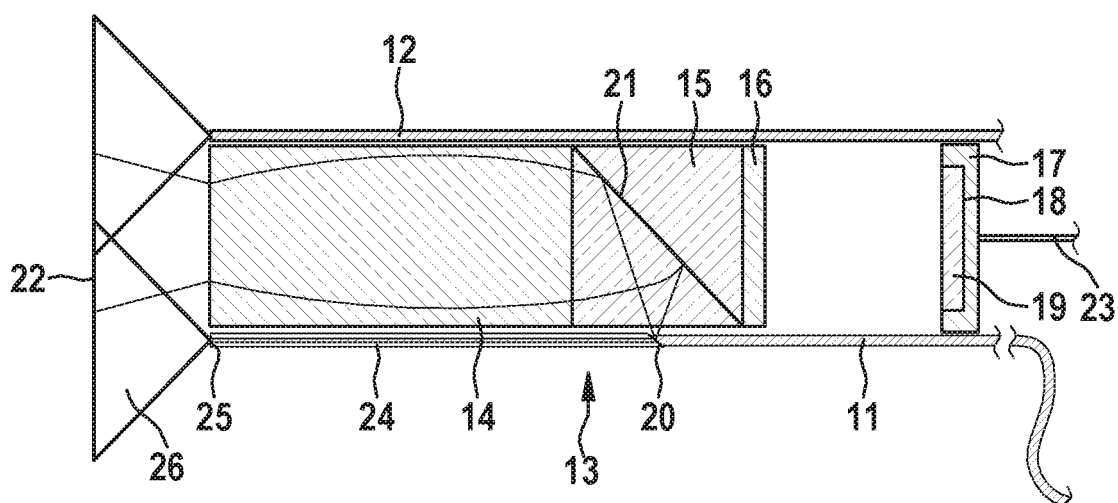
FIG. 2 shows a schematic illustration of an objective with an illumination system of an endoscope in accordance with a first exemplary embodiment of the invention.
Figure 5A:
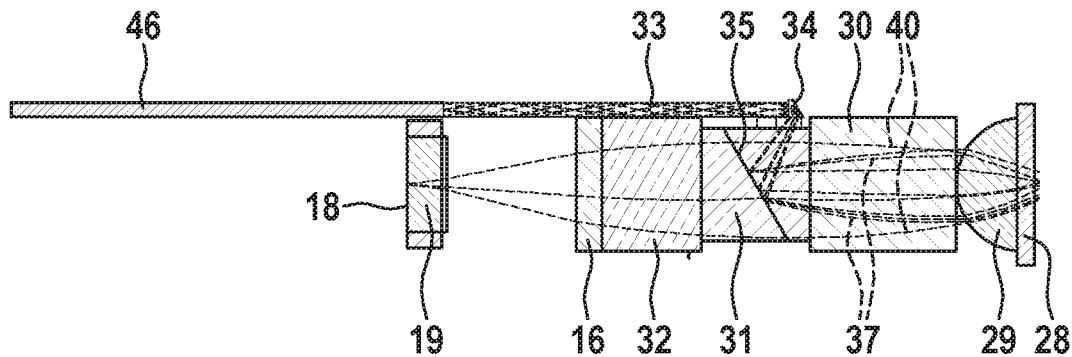
FIGS. 5a to 5d show the distal end region of the endoscope in accordance with FIG. 3.
Figure 5B:
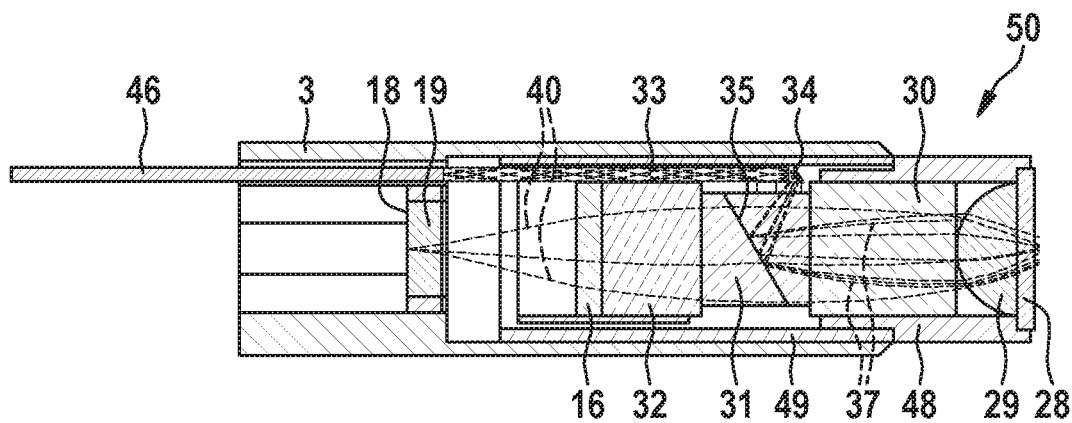
Figure 5C:
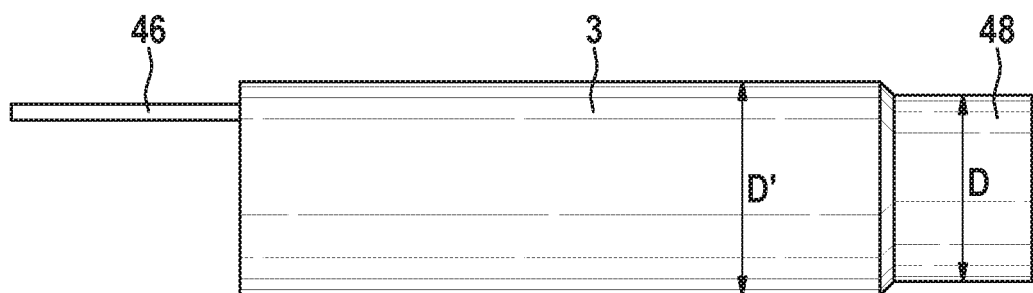
Figure 5D:
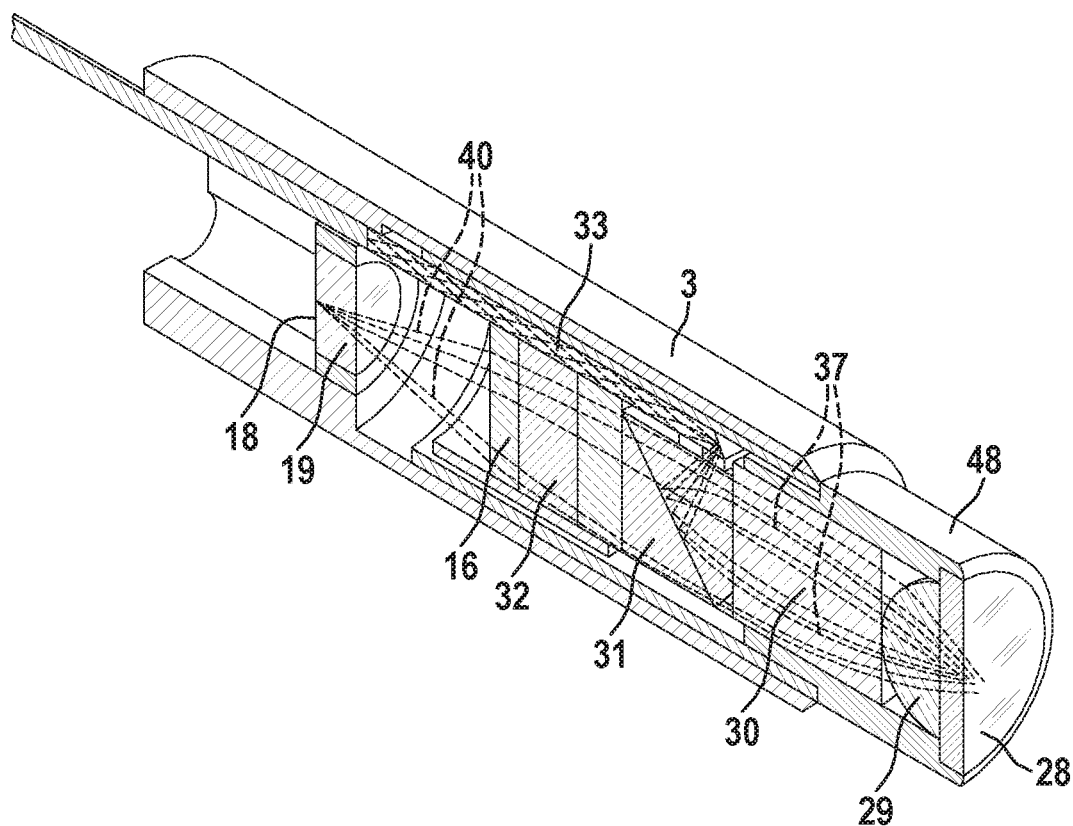

FIG. 2 depicts, in the form of a schematic longitudinal section, the internal configuration of the distal end region 4 of the shaft 2 of the endoscope 1 shown in FIG. 1 in accordance with a first embodiment of the invention, wherein the shaft tube 3 and an objective sleeve surrounding the objective are not shown in FIG. 2. Extending from the handpiece 5 to the distal end region 4 of the endoscope 1 within the shaft 2 are an illumination fiber 11 for forwarding white light and fluorescence excitation radiation and, in the depicted variant of the first embodiment, a further illumination fiber 12 for forwarding a further component of the illumination light to the distal end of the endoscope 1. In the proximal region of the endoscope 1, for example in the handpiece 5, the optical waveguides 11, 12 are connected to the light source unit 10 or, optionally, to a plurality of light source units. The objective 13 of the endoscope comprises a gradient index lens (GRIN lens) 14, a dichroic beam splitter cube 15 and a fluorescence observation filter 16. An electronic image recorder 17 is arranged at the proximal end of the objective 13 in such a way that the sensor area 18 of the image recorder 17, which area adjoins the distal area of the cover glass 19, is in the image plane of the objective 13. As depicted schematically in FIG. 2, the distal end surface of the optical fiber 11 is provided with a partly reflecting deflection surface 20 which is angled at approximately 45° with respect to the longitudinal axis of the optical fiber 11 and which deflects part of the illumination light transmitted by the optical fiber 11 by approximately 90° from an axial direction into a transverse direction in the direction of the dichroic beam splitter cube 15. The beam splitter cube 15 has a splitter surface 21 likewise angled at approximately 45° with respect to the longitudinal direction of the endoscope, which splitter surface deflects the illumination light reflected by the deflection surface 20 back into an axial direction and therefore substantially coaxially with the longitudinal axis of the endoscope or with the optical axis of the objective 13. At the distal end of the endoscope 1, the illumination light deflected by the splitter surface 21 emerges from the objective 13 for illuminating an object field 22. The illumination beam path is indicated symbolically in FIG. 2. Light entering into the objective 13 from the object field 22 is focused by the GRIN lens 14 and focused onto the sensor area 18 of the image recorder 17. For reasons of clarity, the observation beam path from the object field 22 to the sensor area 18 is not shown in FIG. 2. The objective 13 is designed for a magnification in the region from 0.5 to 5, for example approximately 1 or approximately 2.

For fluorescence observation, the deflection surface 20 of the optical fiber 11 is coated dichroically in such a way that the short-wavelength fluorescence excitation radiation is largely reflected in the direction of the beam splitter cube 15. The splitter surface 21 has a dichroic coating which likewise reflects the short-wavelength fluorescence excitation radiation and therefore guides the latter to the object field 22. The fluorescence radiation generated by an object situated in the object field 22, e.g. human or animal tissue, is passed by the dichroic coating of the splitter surface 21 and it thereby reaches the image recorder 17, where a fluorescence image of the object field 22 is created on the sensor area 18. In this case, like in the further exemplary embodiments described below, the image recorder 17 records the fluorescence image and guides it in the form of electric signals by way of the supply and signal cable 23, which is guided within the shaft 2 to the handpiece 5 of the endoscope 1, and by way of the electric cable 6 to the supply apparatus 7 (see FIG. 1).

The dichroic coating of the deflection surface 20 allows some of the illumination light transmitted by the optical fiber 11 to pass, as a result of which this part of the illumination radiation reaches a further optical fiber 24. By means of the latter, the passed part of the illumination radiation is guided as far as the distal end 25 of the endoscope and there it emerges in the form of an illumination light cone 26 for illuminating the object field 22. In the shown example, the light that passed through the deflection surface 20 is suitable for white-light illumination. In the variant of the first embodiment of the invention depicted in FIG. 2, a further component of the illumination light, e.g. likewise white light or radiation suitable for alternative reflectance imaging, can be guided to the distal end 25 of the endoscope by way of the further optical fiber 12 and it can emerge there to illuminate the object field 22. The further optical fiber 12 is not present in another variant of this exemplary embodiment (not depicted here).

Like the fluorescence radiation, the fluorescence excitation radiation reflected or scattered by the object, i.e. the tissue region to be examined, would also be imaged on the sensor area 18 of the image recorder 17 by the GRIN lens 14 without further measures. Since the fluorescence excitation radiation has a substantially higher intensity than the fluorescence radiation of the object, it is necessary, for the purposes of observing the fluorescence radiation, to largely eliminate the fluorescence excitation radiation. This is carried out by the splitter surface 21 of the dichroic beam splitter cube 15, which has a reflecting action for the wavelength range of the fluorescence excitation radiation and therefore eliminates the latter from the beam path of the objective 13. In order to avoid stray light, the objective 13 can have a sleeve (not depicted in FIG. 2) with a light-absorbing inner side. For the purposes of absorbing residual components of the fluorescence excitation radiation possibly passing through the splitter surface 21, a fluorescence observation filter 16 is arranged on the proximal side of the beam splitter cube 15, which fluorescence observation filter can be e.g. an edge filter which is absorbing in the wavelength range of the fluorescence excitation radiation and transmitting in the wavelength range of the fluorescence radiation. The further components of the illumination radiation transmitted by the optical fiber 24 and, optionally, by the further optical fiber 12 are reflected or scattered from the object into the objective and imaged by the GRIN lens 14 onto the sensor area 18 of the image recorder 17. In this case, the image recorder 17 can be embodied, for example, as a color sensor and enable images to be recorded in different wavelength ranges.

FIG. 3 depicts a second embodiment of the invention, likewise as a schematic longitudinal section through the distal end region of the shaft, wherein the shaft tube and the objective sleeve are not shown. The objective 27 depicted in FIG. 3 comprises, from distal to proximal, an optionally multi-layer distal window 28, a planoconvex lens 29, a first GRIN lens 30, a beam splitter cube 31, a second GRIN lens 32 and a fluorescence observation filter 16 placed against the proximal end surface of the second GRIN lens 32. An electronic image recorder (not depicted in FIG. 3) is arranged in such a way that the beams emanating from a distal side of the window 28 are focused on the sensor area 18 of the image recorder, of which only the cover glass 19 is shown in FIG. 3. The objective 27 shown in FIG. 3 is also provided for use in a contact endoscope, by means of which tissue in contact with the window 28 can be examined.

For the purposes of illuminating the tissue, illumination light is guided by way of an optical fiber 33 from the proximal region of the endoscope into the region of the objective 27. The distal end surface of the optical fiber 33 is whetted, in a planar manner, at an angle of 60° with respect to the longitudinal axis of the optical fiber and provided with a mirroring coating. As a result of this, the supplied illumination light is reflected and coupled into the beam splitter cube 31 at an angle of 60° with respect to the longitudinal axis of the objective, the splitter surface 35 of which beam splitter cube is parallel with the distal end surface of the optical fiber 33 and likewise inclined at an angle □=60° in relation to the longitudinal axis of the shaft, said longitudinal axis extending parallel or substantially parallel to the optical axis of the objective 27 or coinciding therewith. In general, the distal end surface of the optical fiber 33 could be whetted, in a planar manner, at an angle of more than 0° and less than 90° with respect to the longitudinal axis of the optical fiber 33, for example, between 40° and 70°, or between 45° and 60°, for example approximately 45° or 60°. In the embodiment shown in FIG. 3, the surface normals of the distal end surface of the optical fiber 33 and of the splitter surface 35 in each case include an angle of approximately 30° with respect to the longitudinal axis of the shaft. The illumination radiation incident on the splitter surface 35 is therefore reflected in the distal axial direction and concentrated by the first GRIN lens 30 and the planoconvex lens 29 onto a small region, for example with a diameter of approximately 250 µm, of the object field arranged at the distal side of the window 28. An axial illumination ray 36, two marginal rays 37 and two rays 38 situated therebetween, which are all in the illumination beam, are depicted in FIG. 3 for illustrative purposes. As can be identified herein, the object field is illuminated from the same direction as, and substantially coaxially with, the observation beam path.

The beam path of the light entering the objective 27 from the object field, i.e. the observation beam path, is depicted in FIG. 3 by an axial ray 39, two marginal rays 40 and two rays 41 lying therebetween. The design of the objective 27 with the planoconvex lens 29 and the GRIN lenses 30, 32 allows a high numerical aperture and, therefore, a high resolution of, for example, 1 to 5 µm. In order to eliminate the reflected or back-scattered excitation light in the case of fluorescence observations, a fluorescence observation filter 16 is provided on the proximal side of the objective 27. As described in relation to FIG. 2, the splitter surface 35 can additionally have a beam-splitting dichroic coating which has a reflecting action for fluorescence excitation radiation and a transmitting action for fluorescence radiation. The second exemplary embodiment can also have the same configuration as the first in respect of the white-light illumination.

As indicated in FIG. 3, a coupling element in the form of a plate 47 cemented with the beam splitter cube 31 and the distal end region of the optical fiber 33 is arranged between the distal end region of the optical fiber 33 and the beam splitter cube 31. The plate 47 is planar on the side adjacent to the beam splitter cube 31 and it has a hollow cylindrical embodiment on the side adjacent to the optical fiber 33, i.e. it is formed as a negative cylindrical lens. As a result of this, reflection losses and refraction on the light path from the optical fiber 33 into the beam splitter cube 31 are avoided or reduced, for example a cylindrical lens effect of the end region of the optical fiber 33.

The distal end region of the optical fiber 33 is depicted with magnification in FIG. 4. As shown in FIG. 4, the deflection surface 34 forms an angle □=120° with the longitudinal axis 42 of the optical fiber 33. The deflection surface 34 has a mirror coating such that the illumination light incident on the deflection surface 34 in the axial direction is reflected in a direction directed obliquely in the proximal direction, as indicated by the arrows 43 in FIG. 4. The optical fiber 33 comprises a light-guiding core 44 which, for example, has a diameter d of approximately 105 µm and cladding 45, surrounding the latter, with for example a diameter d' of approximately 125 µm. Total-internal reflection occurs at the interface between the core 44 and the cladding 45 in the case of small angles with respect to the longitudinal axis 42. The illumination light reflected in an oblique direction by the deflection surface 34 (arrows 43) readily passes through the cladding 45 since total-internal reflection no longer occurs in the case of an angle of approximately 60° with respect to the longitudinal axis 42. The outer envelope 46 of the optical fiber 33 has been removed in the distal end region over a length of e.g. 5 mm.

The arrangement of the components shown schematically in FIGS. 3 and 4 is once again shown in detail in FIGS. 5a to 5d. For the purposes of elucidating the beam path, two marginal rays 37 of the illumination beam and two marginal rays 40 of the observation beam path and respectively one or more further rays are shown. The window 28, the plano-convex lens 29 and the first GRIN lens 30 are inserted into a first sleeve 48 which, together with a second sleeve 49, in which the beam splitter cube 31, the second GRIN lens 32, the fluorescence observation filter 16 and the distal end region of the optical waveguide 33 are received, forms an objective sleeve 50. The objective sleeve 50 is inserted into the shaft tube 3 of the endoscope and it protrudes from the latter on the distal side. In the shown exemplary embodiment, the external diameter D of the objective sleeve 50 or of the first sleeve 49 is approximately 1.4 mm and the external diameter D' of the shaft tube 3 is approximately 1.6 mm.

Figure 6:
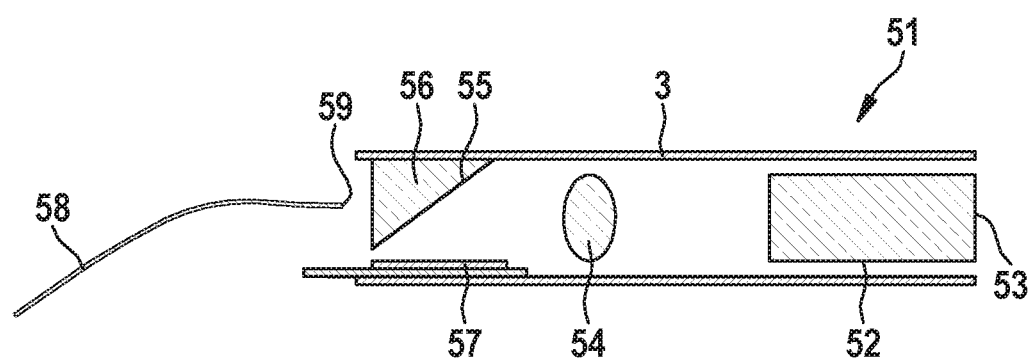
FIG. 6 shows the distal end region of an endoscope in accordance with a third exemplary embodiment of the invention in a schematic form.

FIG. 6 shows, in the form of a schematic longitudinal section, the distal end region of the shaft of an endoscope in accordance with a third exemplary embodiment of the invention. In this embodiment, the objective 51 received in the shaft tube 3 of the endoscope comprises a GRIN lens 52 which, with the distal side thereof, forms the contact surface 53 for tissue to be examined. Together with a further lens 54, the GRIN lens 52 images the object field, which is formed by the contact surface 53, on the sensor area of an electronic image recorder 57 arranged in a "lying" fashion in the shaft tube 3 by way of a splitter surface 55, coated in a partly reflecting manner, of a micro-prism 56. An illumination fiber 58 supplies illumination radiation from the proximal region of the endoscope, said illumination radiation emerging in the axial distal direction through the distal end surface 59, whetted in a planar manner, of the illumination fiber 58. The illumination radiation at least partly passes through the splitter surface 55 and it is forwarded to the contact surface 53 by the lens 54 and the GRIN lens 52. For the purposes of fluorescence examinations, the splitter surface 55 can have such a dichroic coating that said splitter surface transmits the fluorescence excitation radiation transmitted by the illumination fiber 58 and reflects the fluorescence radiation generated by the tissue. In respect of white-light illumination, the third exemplary embodiment can likewise be configured like the first. The optical elements of the objective and the image recorder can be received in an objective sleeve (not shown here).

For reasons of clarity, not all reference signs are depicted in all figures. Reference signs not explained in respect of one figure have the same meaning as in the remaining figures.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

What is claimed is:

1. An endoscope comprising:
   an elongate shaft;
   an optical waveguide for forwarding illumination radiation from a proximal region to a distal end region of the shaft; and
   an objective arranged in the distal end region of the shaft for generating an image of an object field in an image plane, the objective including a beam splitter that is spaced apart from the optical waveguide in a radial direction of the optical waveguide;
   wherein an emergence portion of the optical waveguide comprises an at least partly reflecting deflection surface that is at an angle to a longitudinal axis of the optical waveguide, and in a forwarding direction of the illumination radiation, the emergence portion is positioned upstream of the beam splitter, such that at least a portion of the illumination radiation is forwarded from the emergence portion to the beam splitter to illuminate the object field.

2. The endoscope according to claim 1, wherein the emergence portion is adapted to forward at least the portion of the illumination radiation in an axial direction to the beam splitter and the beam splitter is adapted to pass at least a portion of the illumination radiation in an axial direction to illuminate the object field and to deflect at least a portion of the radiation coming from the object field.

3. The endoscope according to claim 1, wherein the emergence portion deflects at least the portion of the illumination radiation to the beam splitter and the beam splitter deflects at least a portion of the illumination radiation to the object field and passes at least a portion of the radiation coming from the object field in an axial direction.

4. The endoscope according to claim 1, wherein the optical waveguide comprises at least one optical fiber and the deflection surface is an end surface of the at least one optical fiber that is at an angle to the longitudinal axis of the optical fiber.

5. The endoscope according to claim 4, wherein the deflection surface and a splitter surface of the beam splitter are substantially parallel to one another.

6. The endoscope according to claim 5, wherein the at least one optical fiber extends substantially parallel to the shaft of the endoscope, and wherein the surface normals of the deflection surface and the splitter surface each include an angle of approximately 30° to approximately 45° with a longitudinal axis of the shaft of the endoscope.

7. The endoscope according to claim 1, wherein the deflection surface has a dichroic beam-splitting embodiment to pass at least a portion of the illumination radiation, and wherein a further optical waveguide is provided to forward the passed part of the illumination radiation for further illumination of the object field.

8. The endoscope according to claim 1, further comprising an additional optical waveguide for forwarding further illumination radiation to the distal end region of the shaft for further illumination of the object field.

9. The endoscope according to claim 1, wherein an optical coupling element is arranged between the emergence portion and the beam splitter.

10. The endoscope according to claim 1, wherein the beam splitter is a prism beam splitter or a beam splitter cube or a beam splitter plate.

11. The endoscope according to claim 1, wherein the beam splitter is a polarizing beam splitter.

12. The endoscope according to claim 1, wherein the beam splitter has a dichroic beam-splitting embodiment.

13. The endoscope according to claim 1, wherein the objective comprises at least one GRIN lens.

14. The endoscope according to claim 1, wherein a magnification defined as ratio of image size to object size has a value between 0.5 and 5.

15. The endoscope according to claim 1, wherein the endoscope is a contact endoscope.

16. The endoscope according to claim 1, wherein the beam splitter is positioned between a first GRIN lens and a second GRIN lens.

17. The endoscope according to claim 1, wherein the longitudinal axis of the optical waveguide is offset from a longitudinal axis of the objective.

18. The endoscope according to claim 1, wherein the emergence portion is adapted to forward at least the portion of the illumination radiation to the beam splitter and the beam splitter couples at least a portion of the illumination radiation in an axial direction to illuminate the object field.

19. An endoscope comprising:
an elongate shaft;
an objective arranged in a distal end region of the shaft for generating an image of an object field in an image plane, the objective comprising a beam splitter;
an optical waveguide for forwarding illumination radiation from a proximal region to the distal end region of the shaft; and
wherein an emergence portion of the optical waveguide comprises an at least partly reflecting deflection surface that is at an angle to a longitudinal axis of the optical waveguide, and in a forwarding direction of the illumination radiation, the emergence portion is positioned upstream of the beam splitter, such that at least a portion of the illumination radiation is forwarded from the emergence portion to the beam splitter to illuminate the object field,
wherein an optical coupling element is arranged between the emergence portion and the beam splitter, and
wherein one surface of the optical coupling element directly contacts the beam splitter and another surface of the optical coupling element directly contacts an optical fiber of the optical waveguide.

20. An endoscope comprising:
an elongate shaft;
an objective arranged in a distal end region of the shaft for generating an image of an object field in an image plane, the objective comprising a beam splitter;
an optical waveguide for forwarding illumination radiation from a proximal region to the distal end region of the shaft; and
wherein the optical waveguide includes an emergence portion and, in a forwarding direction of the illumination radiation, the emergence portion of the optical waveguide is positioned upstream of the beam splitter such that at least a portion of the illumination radiation is forwarded from the emergence portion to the beam splitter to illuminate the object field, and
wherein the emergence portion comprises an at least partly reflecting deflection surface that is at an angle to a longitudinal axis of the optical waveguide.

* * * * *